US 6,589,486 B1

(12) United States Patent
Spanton

(10) Patent No.: US 6,589,486 B1
(45) Date of Patent: Jul. 8, 2003

(54) AIR PURIFYING APPARATUS AND METHOD

(75) Inventor: John B Spanton, Osceola, WI (US)

(73) Assignee: Osceola Specialty Products, Osceola, WI (US)

( * ) Notice: Subject to any disclaimer, the term of this patent is extended or adjusted under 35 U.S.C. 154(b) by 0 days.

(21) Appl. No.: 09/470,694

(22) Filed: Dec. 21, 1999

Related U.S. Application Data

(60) Provisional application No. 60/113,024, filed on Dec. 21, 1998.

(51) Int. Cl.[7] .............................. A61L 9/00; A61L 9/20
(52) U.S. Cl. .................. 422/121; 422/120; 422/186.07; 96/16; 96/224
(58) Field of Search ............................ 422/186.07, 121, 422/120, 24, 3, 5; 96/16, 140, 224, 55; 95/90

(56) References Cited

U.S. PATENT DOCUMENTS

| 3,653,185 A | | 4/1972 | Scott et al. | |
|---|---|---|---|---|
| 3,750,370 A | | 8/1973 | Brauss et al. | |
| 4,849,115 A | * | 7/1989 | Cole et al. | 210/192 |
| 4,917,862 A | * | 4/1990 | Kraw et al. | 422/122 |
| 4,990,313 A | | 2/1991 | Pacosz | |
| 5,112,370 A | | 5/1992 | Gazzano | |
| 5,160,513 A | | 11/1992 | Koves | |
| 5,330,722 A | | 7/1994 | Pick et al. | |
| 5,334,347 A | | 8/1994 | Hollander | |
| 5,492,557 A | | 2/1996 | Vanella | |
| 5,523,057 A | * | 6/1996 | Mazzilli | 250/436 |
| 5,833,740 A | | 11/1998 | Brais | |
| 5,866,076 A | * | 2/1999 | Fencl et al. | 250/454.11 |
| 5,933,702 A | * | 8/1999 | Goswami | 422/186.3 |
| 6,221,314 B1 | * | 4/2001 | Bigelow | 250/432 R |

OTHER PUBLICATIONS

American Ultraviolet Company, Advertisement, 1 page.

* cited by examiner

Primary Examiner—Hien Tran
(74) Attorney, Agent, or Firm—Skinner and Associates

(57) ABSTRACT

The apparatus and method of the present invention are suitable for use in the HVAC system of a building or dwelling such as a home or small commercial building. The apparatus and method cleans, purifies and deodorizes air in the building or dwelling. The air purifying apparatus comprises the following basic components: a UV germicidal lamp, an ozone generator, an air flow sensor, a control system, a status display system, a coupling system to connect the apparatus to an HVAC system, and a power system.

6 Claims, 5 Drawing Sheets

AIR PURIFYING APPARATUS AND METHOD

CROSS-REFERENCE TO RELATED APPLICATIONS, IF ANY

This application claims the benefit under 35 U.S.C. §119 (e) of co-pending provisional application Ser. No. 60/113,024, filed Dec. 21, 1998, which is hereby incorporated by reference.

37 C.F.R. §1.71(e) AUTHORIZATION

A portion of the disclosure of this patent document contains material which is subject to copyright protection. The copyright owner has no objection to the facsimile reproduction by anyone of the patent document or the patent disclosure, as it appears in the Patent and Trademark Office patent file or records, but otherwise reserves all copyright rights whatsoever.

STATEMENT REGARDING FEDERALLY SPONSORED RESEARCH OR DEVELOPMENT

Not applicable.

REFERENCE TO A MICROFICHE APPENDIX, IF ANY

Not applicable.

BACKGROUND OF THE INVENTION

1. Field of the Invention

The present invention relates, generally, to air cleaning apparatus and method. More particularly, the invention relates to an apparatus and method for purifying and cleaning air in a building or dwelling. The invention has particular utility in purifying air in homes and small buildings which utilize a forced air heating and/or cooling system.

2. Background Information

The state of the art includes various devices and methods for purifying air in a building or dwelling.

Prior art devices and methods are believed to have significant limitations and shortcomings.

The present invention provides an air purification apparatus and method which are believed to constitute an improvement over the prior art.

BRIEF SUMMARY OF THE INVENTION

Ultraviolet (UV) radiation is germicidal, that is, it kills microorganisms, including both bacteria and viruses. Microorganisms can cause disease or act as allergens. The apparatus of this invention generates high frequency UV-c radiation and directs it to a predetermined location in a standard forced air building heating, ventilating and/or air conditioning system (HVAC), whereby microorganisms are killed and the air is therefore cleaned.

Ozone is a naturally occurring substance which cleans air and removes odors from air. Ozone in combination with UV radiation destroys microorganisms which are not killed by the UV radiation. The apparatus of this invention generates ozone in a safe and balanced concentration of 0.2–0.3 parts per million. This is effective to clean the air put through a standard forced air building heating, ventilating and/or air conditioning system. Ozone also destroys odors without simply masking them.

The present invention provides an apparatus and method for purifying air which comprises a UV germicidal lamp, an ozone generator, an air flow sensor, a control system, a status display system, a coupling system to connect the apparatus to an HVAC system, and a power system.

The features, benefits and objects of this invention will become clear to those skilled in the art by reference to the following description, claims, and drawings.

DETAILED DESCRIPTION

Referring to FIGS. 1–8, an example of the preferred embodiment of the air purifying apparatus of the present invention is illustrated.

Figure 1:
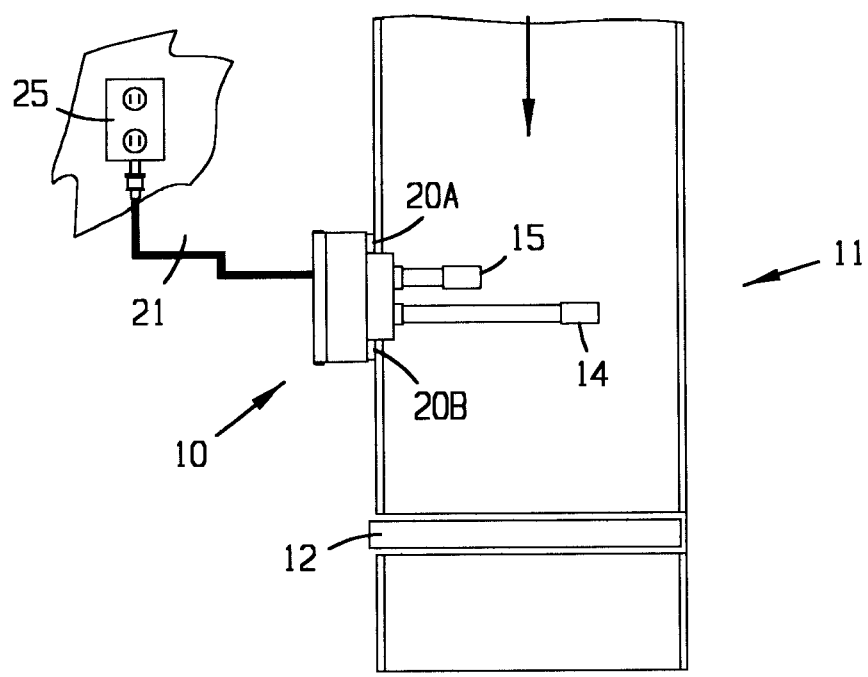
FIG. 1 is a crossectional view of a building heating system with the air purifying apparatus of the present invention operatively disposed therein.
Figure 2:
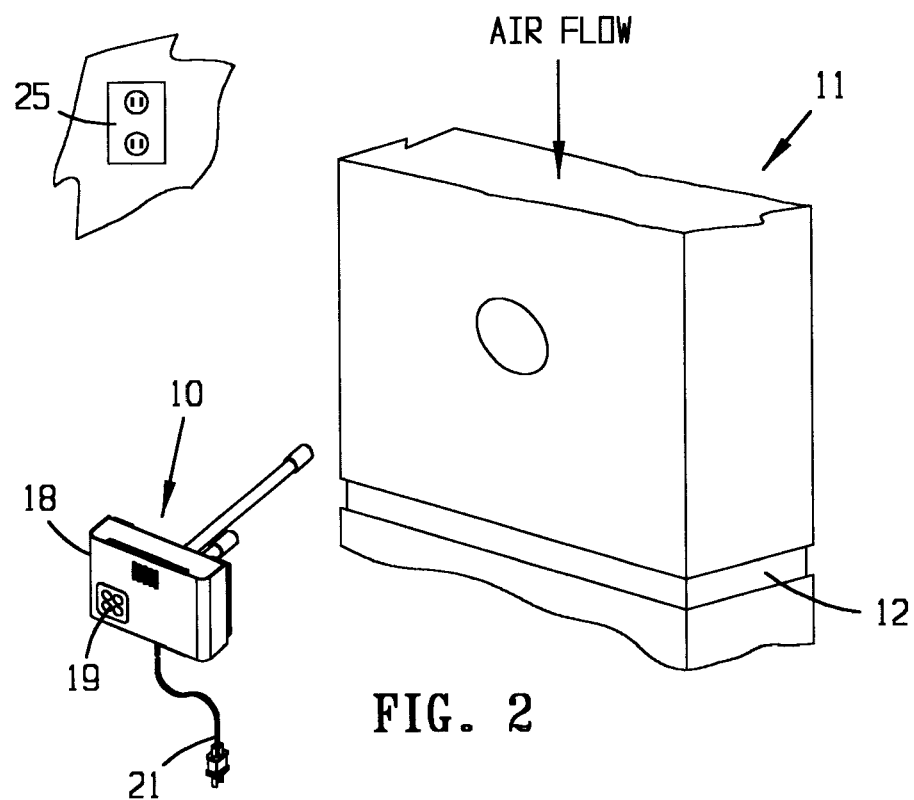
FIG. 2 is a perspective view of the heating system with the air purifying apparatus in position for attachment.
Figure 3:
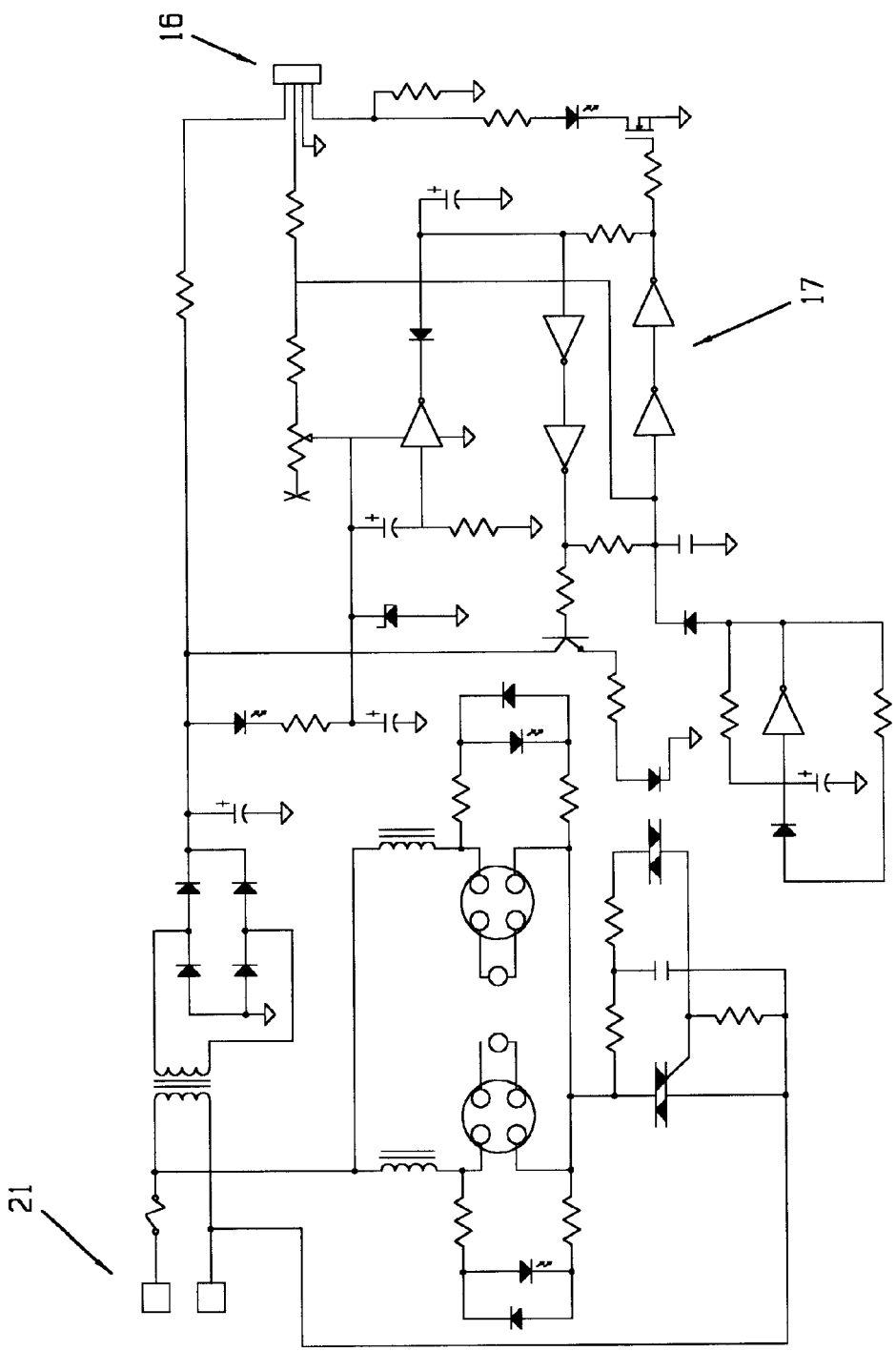
FIG. 3 is a schematic of the circuitry of the air purifying apparatus.
Figure 4:
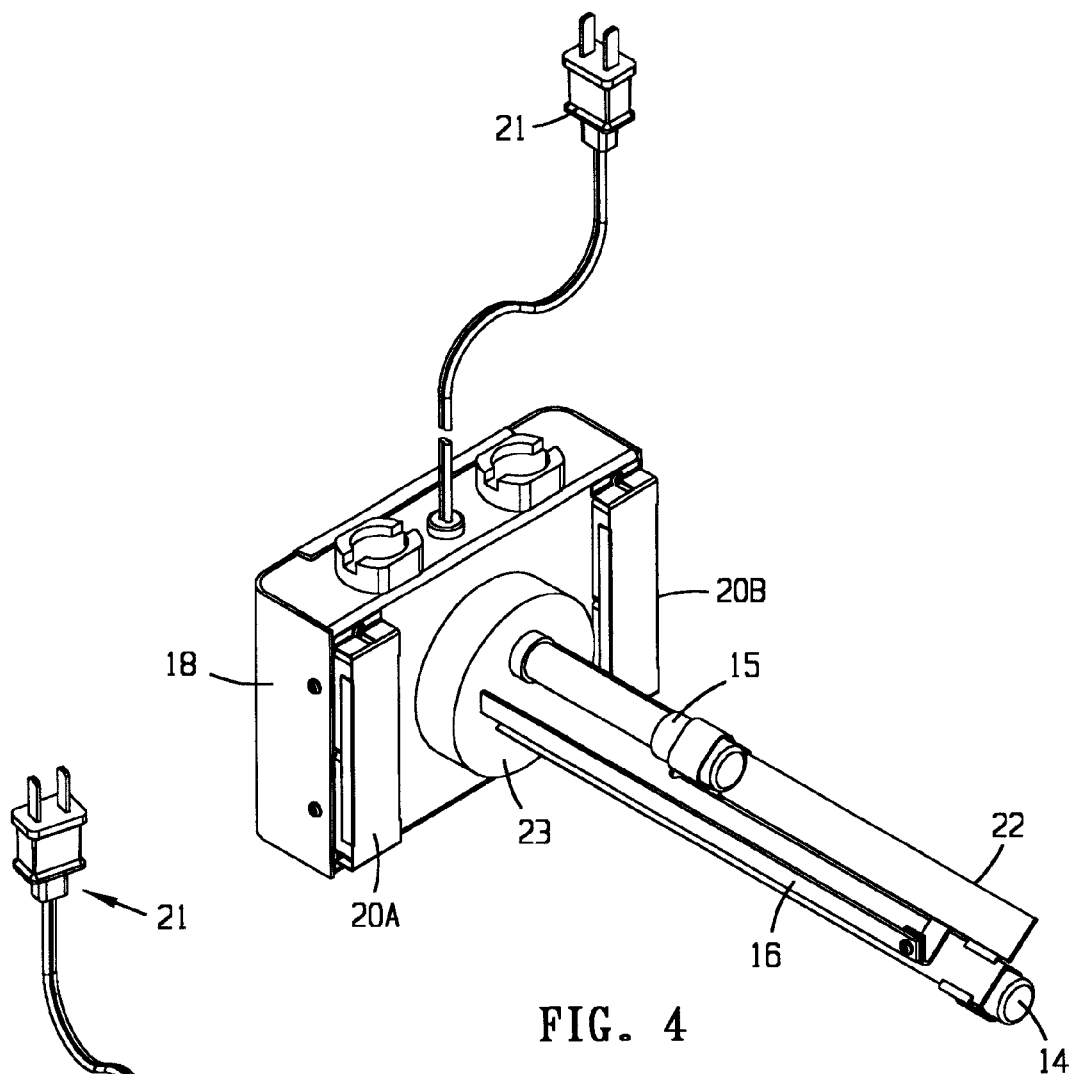
FIG. 4 is perspective view of the air purifying apparatus.
Figure 5:
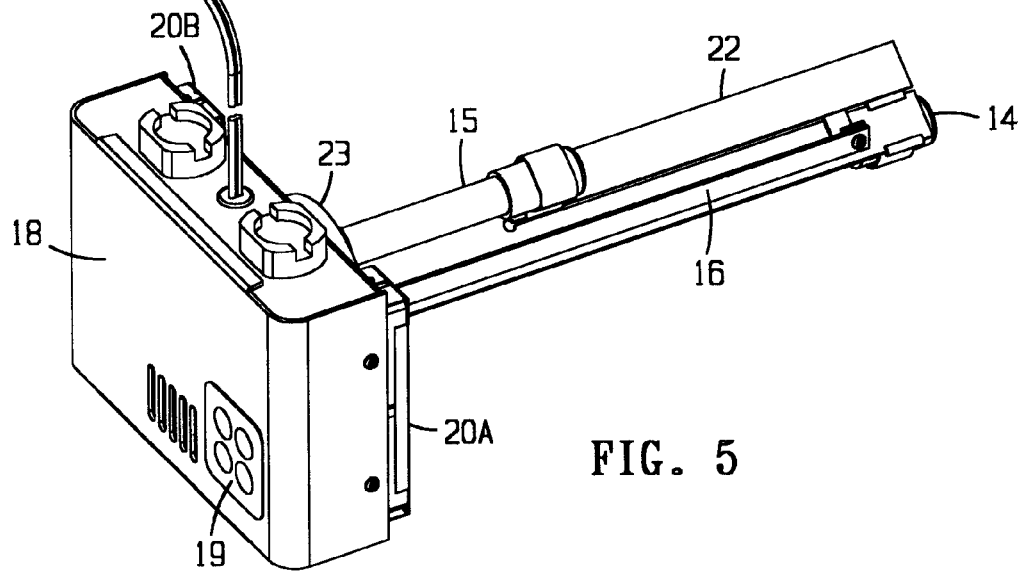
FIG. 5 is another perspective view of the air purifying apparatus, taken, generally, from the opposite end with respect to FIG. 4.
Figure 6:
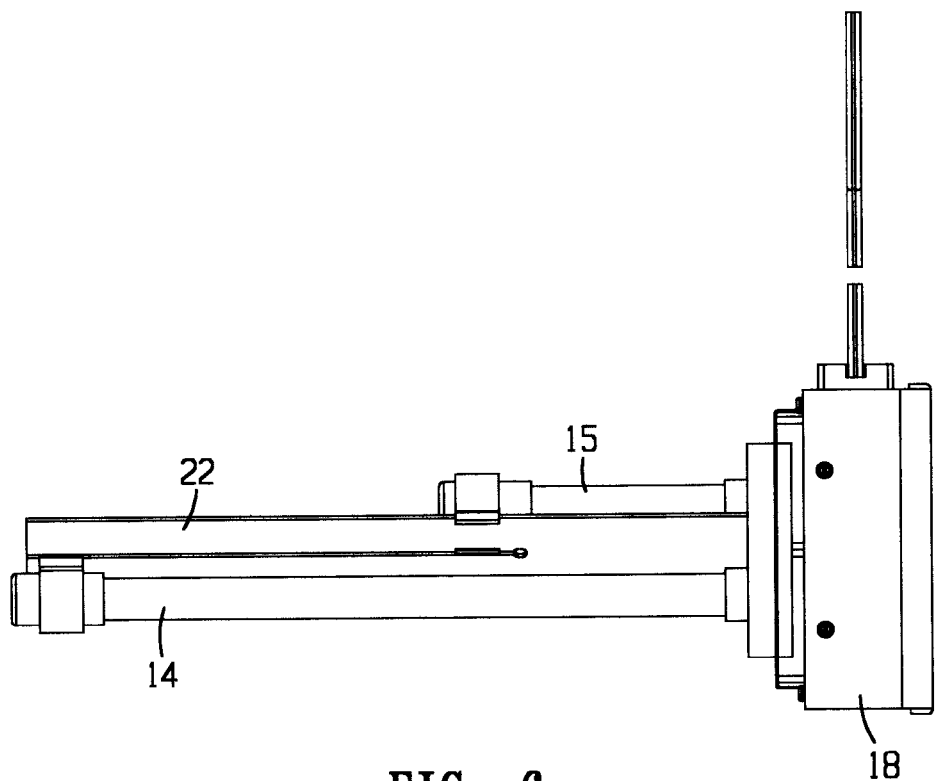
FIG. 6 is a side view of the air purifying apparatus.
Figure 7:
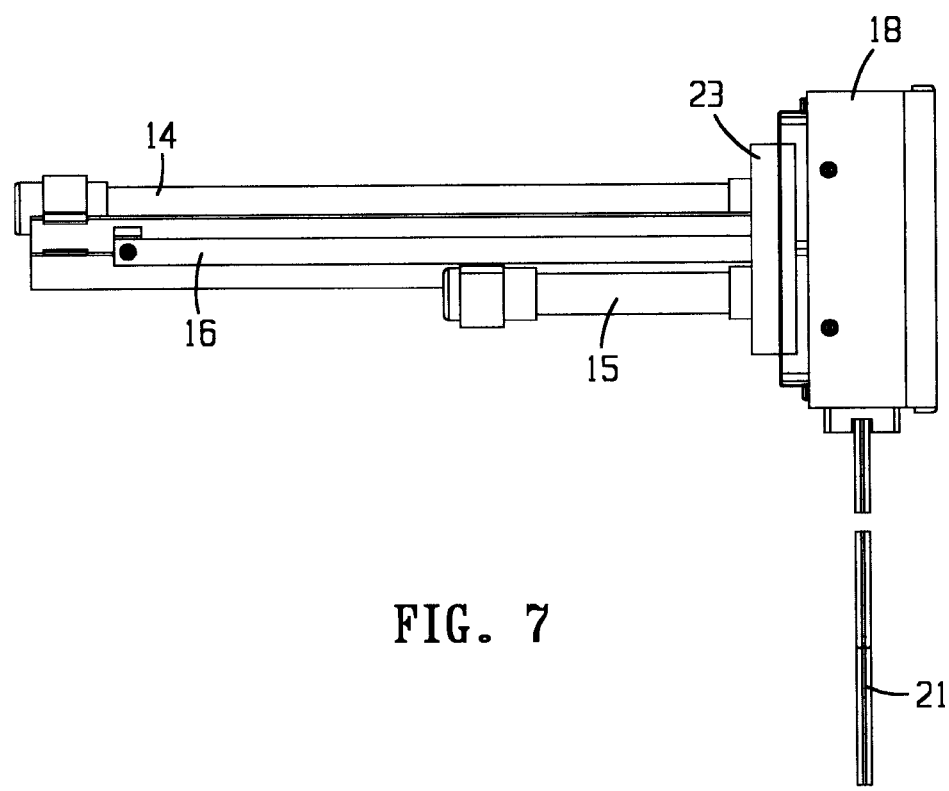
FIG. 7 is an opposing side view of the air purifying apparatus.
Figure 8:
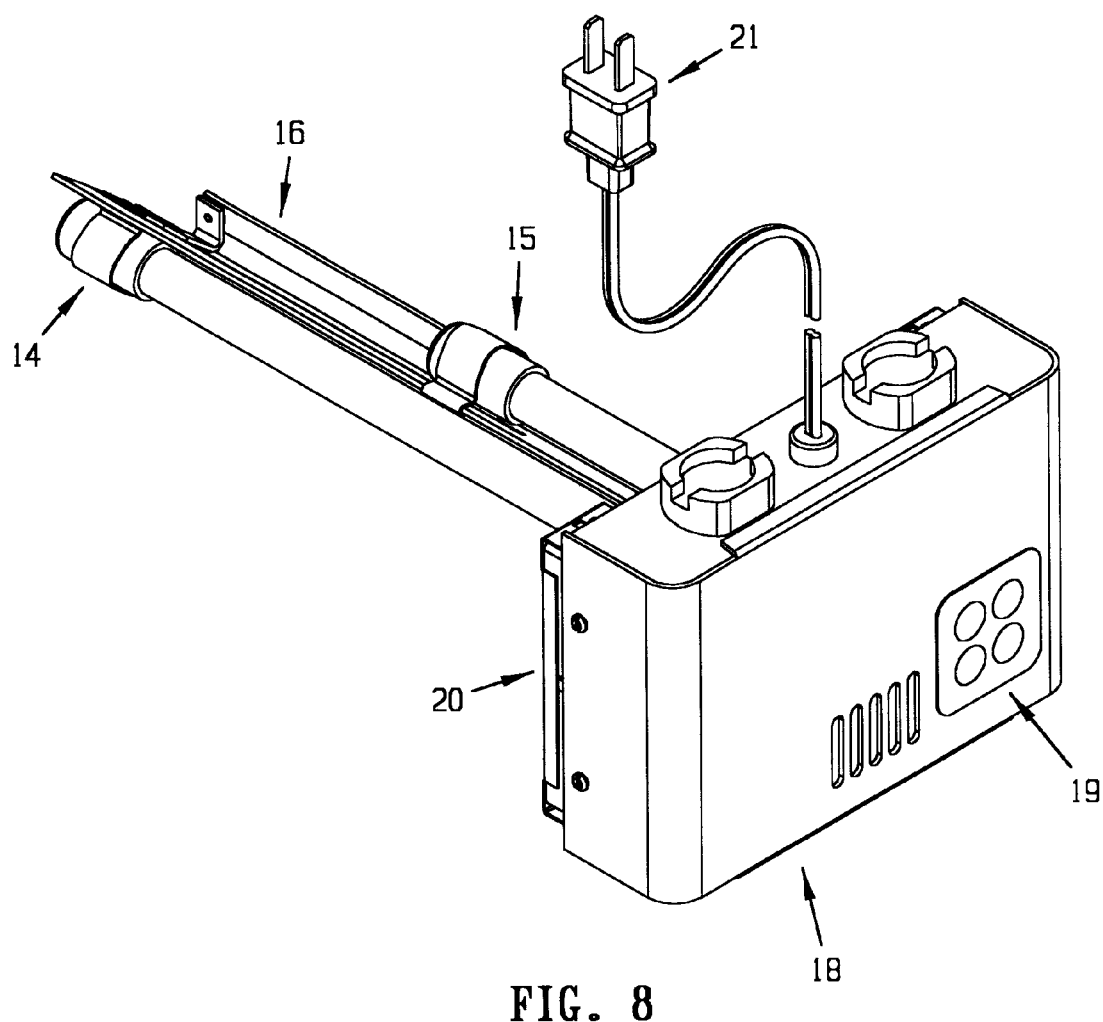
FIG. 8 is another perspective view of the air purifying apparatus.

Referring to FIGS. 1 and 2, the apparatus and method of the present invention are suitable for use in the HVAC system of a building or dwelling such as a home or small commercial building. The apparatus and method cleans, purifies and deodorizes air in the building or dwelling. The apparatus 10 is disposed on an HVAC system 11. The system is installed via the following procedure:

1. Locate the cold air return duct entering the HVAC system or central furnace.
2. Center and tape a mounting template or equivalent structure on the cold air return duct approximately at least six (6) inches away from the furnace filter 12, which is the preferred area to be exposed to germicidal UV radiation.
3. Drill or cut a 3 inch diameter hole 13 in the duct. The hole must be wide enough to accept the lamp elements 14 and 15. The lamp element should not contact any portion of the duct.
4. Mount the lamp elements across the duct to occupy the largest area inside the duct. Remove the template, if used, and insert the lamp elements into the hole, making sure that the flow sensor is properly positioned. No screws or fasteners are needed due to the system magnets.
5. Plug the power cord 16 into a common 110V outlet 25.

Referring also to FIGS. 3–8, the air purifying apparatus; comprises the following basic components: a UV germicidal lamp 14, an ozone generator lamp 15, an air flow sensor 16, each of the above preferably being coupled to a support structure 22, control system circuitry 17 communicatively connected to each of the components above and being disposed in a housing 18, a status display system 19 connected to the control system 17, coupling magnets 20 a and b disposed on the housing to connect the apparatus to an HVAC system, and a power cord 21 connected to the control system. The housing preferably has a sealing collar 23 disposed about the base of the lamps to seal any gap in the HVAC hole and the apparatus.

The device has the following activation states which are indicated by a status display system as follows:

1. Red Light: Power On
2. Green Light:
   Blinking: Indicates stand by/system check condition. No air flow is detected. Unit is in an operational ready state.
   Solid: Unit detects air flow and senses that an HVAC central fan has been activated. Lamp elements will light within approximately 30–60 seconds
3. Amber Lights: Two, one for each lamp element. As a safety feature, the indicator lights will blink rapidly prior to each activation of the apparatus. When lamp elements are activated, both indicator lights are brightly lit.

| QUANTITY | SYMBOL(S)/ DESCRIPTION | DESCRIPTION/VALUE |
|---|---|---|
| 3 | C2, C3 | 220 ufd |
| 1 | C5 | 100 ufd |
| 1 | C6 | 0.1 |
| 1 | C7 | 0.01 |
| 4 | D1, D2, D3 D4 | 1N4004 |
| 1 | D5 | Red LED |
| 2 | D7, D6 | Yellow LED |
| 1 | D8 | Green LED |
| 1 | D9 | 1N4740A |
| 5 | D10, D11, D12, D13, D14 | 1N4148 |
| 1 | F1 | Fuse |
| 2 | J1, J2 | Spade Lug |
| 1 | J3 | Probe |
| 2 | L1, L2 | Flash |
| 2 | L2, L4 | Sanitizer |
| 1 | Q1 | Triac |
| 1 | Q2 | IRF610 |
| 1 | Q3 | MPSA13 |
| 1 | R1 | 10K |
| 1 | R2 | 470K |
| 5 | R3, R16, R17, R18, R19 | 4.7K |
| 5 | R4, R9, R10, R12, R14 | 1K |
| 4 | R5, R11, R20, R20, R22 | 100 |
| 4 | R6, R7, R8, R13 | 27K |
| 1 | R15 | 470 |
| 1 | R21 | 220 |
| 1 | T1 | 12 Volt pri |
| 2 | T2, T3 | Ballast |
| 1 | U1 | CD40106 |
| 1 | U2 | MOC3009 |
| 1 | Socket | 14 DIP Socket |
| 1 | F1X | Fuse Holder |
| 4 | Spacer | Spacer for LED standoff |
| 4 | Socket | Socket Pins for Probe J3 |
| 8 | Socket | Socket Pins for Lamps L2, L4 |

The descriptions above and the accompanying materials should be interpreted in the illustrative and not the limited sense. While the invention has been disclosed in connection with the preferred embodiment or embodiments thereof, it should be understood that there may be other embodiments which fall within the scope of the invention.

The invention claimed is:

1. An air cleaning apparatus for use with an HVAC system having a metal airflow duct, comprising:
   a. a housing having an exterior coupling surface adapted for placement adjacent to the exterior of the HVAC system airflow duct;
   b. at least one magnet connected to the coupling surface of the housing, the at least one magnet being adapted for quickly coupling and uncoupling the housing to the HVAC system airflow duct without the need for tools;
   c. a UV lamp connected to the housing and extending a predetermined distance from the exterior coupling surface, the UV lamp being adapted for insertion into and retraction from the HVAC system airflow duct and biologically clean air flowing therein;
   d. an ozone generator lamp connected to the housing and extending a predetermined distance from the exterior coupling face, the ozone generator lamp being adapted for insertion into and retraction from the HVAC system airflow duct and chemically clean air flowing therein;
   e. an air flow sensor connected to the housing and extending a predetermined distance from the exterior coupling surface, the air flow sensor being adapted for insertion into and retraction from the HVAC system airflow duct, the airflow sensor providing information for automatic control of the UV lamp and ozone generator lamp;
   f. a control system disposed in the housing and being communicatively connected to the UV lamp, ozone generator lamp and air flow sensor; and
   g. a lamp status indicator communicatively connected to the control system for alerting the user when the UV lamp and ozone generator lamp are "on" and it is not safe to retract the lamps from the HVAC airflow duct.

2. The apparatus of claim 1 further comprising a power cord connected to the control system.

3. The apparatus of claim 1 further comprising a sealing collar disposed about a predetermined base portion of said UV lamp and a base portion of said ozone generator lamp at said housing exterior coupling surface.

4. The apparatus of claim 1, wherein the lamp status indicator is a visual indicator comprising at least one light source, the light source providing an indication signal representing that at least one lamp will light in a predetermined period of time and providing an indication signal representing that at least one lamp is "on".

5. An air cleaning apparatus for use with an HVAC system having a metal airflow duct, comprising:
   a. a housing having an exterior coupling surface adapted for placement adjacent to the exterior of the HVAC system airflow duct;
   b. at least one magnet connected to the coupling surface of the housing, the at least one magnet being adapted for coupling the housing to the HVAC system airflow duct;
   c. a UV lamp connected to the housing and extending a predetermined distance from the exterior coupling surface, the UV lamp being adapted for insertion into and retraction from the HVAC system airflow duct and biologically clean air flowing therein;
   d. an ozone generator lamp connected to the housing and extending a predetermined distance from the exterior coupling surface, the ozone generator lamp being adapted for insertion into and retraction from the HVAC system airflow duct and chemically clean air flowing therein;
   e. an air flow sensor connected to the housing and extending a predetermined distance from the exterior coupling surface, the air flow sensor being adapted for insertion into and retraction from the HVAC system airflow duct, the airflow sensor providing information for automatic control of the UV lamp and ozone generator; and f. a control system disposed in the housing and being communicatively connected to the UV lamp, ozone generator lamp and air flow sensor.

6. An air cleaning apparatus for use with an HVAC system having a metal airflow duct, comprising:

a. a housing having an exterior coupling surface adapted for placement adjacent to the exterior of the HVAC system airflow duct;

b. a UV lamp connected to the housing and extending a predetermined distance from the exterior coupling surface, the UV lamp being adapted for insertion into and retraction from the HVAC system airflow duct and biologically clean air flowing therein;

c. an ozone generator lamp connected to the housing and extending a predetermined distance from the exterior coupling surface, the ozone generator lamp being adapted for insertion into and retraction from the HVAC system airflow duct and chemically clean air flowing therein;

d. an air flow sensor connected to the housing and extending a predetermined distance from the exterior coupling surface, the air flow sensor being adapted for insertion into and retraction from the HVAC system airflow duct, the airflow sensor providing information for automatic control of the UV lamp and ozone generator;

e. a control system disposed in the housing and being communicatively connected to the UV lamp, ozone generator lamp and air flow sensor; and f. a lamp status indicator communicatively connected to the control system for providing visual information to the user on the status of the UV lamp and ozone generator lamp, the lamp status indicator comprising at least one light source, the light source providing an indication signal representing that at least one lamp will light in a predetermined period of time and providing an indication signal representing that at least one lamp is "on" and it is not safe to retract the lamps from the HVAC airflow duct.

* * * * *